United States Patent
Zhu et al.

(10) Patent No.: US 9,242,927 B2
(45) Date of Patent: Jan. 26, 2016

(54) PROCESS FOR THE MANUFACTURE OF N-ACYLBIPHENYL ALANINE

(71) Applicants: Guoliang Zhu, Zhejiang (CN); Desong Shi, Zhejiang (CN); Junhui Wei, Zhejiang (CN); Fengfeng Tao, Zhejiang (CN)

(72) Inventors: Guoliang Zhu, Zhejiang (CN); Desong Shi, Zhejiang (CN); Junhui Wei, Zhejiang (CN); Fengfeng Tao, Zhejiang (CN)

(73) Assignees: ZHEJIANG JIUZHOU PHARMACEUTICAL CO., LTD, Zhejiang (CN); NOVARTIS AG, Basel (CH)

(*) Notice: Subject to any disclaimer, the term of this patent is extended or adjusted under 35 U.S.C. 154(b) by 0 days.

(21) Appl. No.: 14/163,526

(22) Filed: Jan. 24, 2014

(65) Prior Publication Data

US 2014/0142320 A1      May 22, 2014

Related U.S. Application Data

(63) Continuation of application No. 13/497,544, filed as application No. PCT/CN2010/071243 on Mar. 23, 2010, now abandoned.

(30) Foreign Application Priority Data

Sep. 23, 2009   (WO) ................ PCT/CN2009/074125

(51) Int. Cl.
| | | |
|---|---|---|
| C07C 235/00 | (2006.01) |
| C07C 231/10 | (2006.01) |
| C07C 231/12 | (2006.01) |
| C07C 233/47 | (2006.01) |
| C07C 235/34 | (2006.01) |
| C07C 233/87 | (2006.01) |
| C07D 263/18 | (2006.01) |
| C07D 263/42 | (2006.01) |

(52) U.S. Cl.
CPC ............ *C07C 235/00* (2013.01); *C07C 231/10* (2013.01); *C07C 231/12* (2013.01); *C07C 233/47* (2013.01); *C07C 233/87* (2013.01); *C07C 235/34* (2013.01); *C07D 263/18* (2013.01); *C07D 263/42* (2013.01)

(58) Field of Classification Search
None
See application file for complete search history.

(56) References Cited

U.S. PATENT DOCUMENTS

| | | |
|---|---|---|
| 4,612,388 A | 9/1986 | Mita et al. |
| 2004/0180943 A1 | 9/2004 | Augelli-Szafran et al. |
| 2012/0016151 A1 | 1/2012 | Zhu et al. |

FOREIGN PATENT DOCUMENTS

| | | |
|---|---|---|
| CN | 101555211 | 10/2009 |
| EP | 0212617 | 3/1987 |
| GB | 2354440 A | 3/2001 |
| JP | 60185752 A2 | 9/1985 |
| JP | 2003261522 A | 9/2003 |
| WO | 98/47876 | 10/1998 |
| WO | 2004002977 | 1/2004 |
| WO | 2010034236 | 4/2010 |

OTHER PUBLICATIONS 4-([1,1-biphenyl]-4ylmethylene)-2-methyl-5(4H)-oxazolone, RN 909768-56-5, Database Registry [online]. Columbus, Phio, US: Chemical Abstracts Service. Retrieved on Oct. 6, 1989.
Khan, Khalid Mohammed et al., 2009, "Synthesis and antibacterial and antifungal activity of 5-substitued imidazolones." Letters in Drug Design & Discovery. vol. 6, No. 1, pp. 69-77.
Petkova, Irina et al., 2009, "Tuning the excited-state dynamics of GFP-inspired imidazolone derivatives." J. Phys. Chem. A, vol. 114, pp. 10-20.
Gary M. K. et al., 1995, "Dicarboxylic acid dipeptide neutral endopeptidase inhibitors." J. Med. Chem., vol. 38, No. 10, pp. 1689-1700.
Yuichiro Yabe et al., 1976, Chem. Pharm. Bull, 24(12), 3149-3157.

*Primary Examiner* — Kamal Saeed
(74) *Attorney, Agent, or Firm* — David Kurlandsky

(57) ABSTRACT

The invention relates to a novel process, novel process steps and novel intermediates useful in the synthesis of pharmaceutically active compounds, in particular neutral endopeptidase (NEP) inhibitors.

13 Claims, No Drawings

PROCESS FOR THE MANUFACTURE OF N-ACYLBIPHENYL ALANINE

FIELD OF THE INVENTION

The invention relates to a novel process, novel process steps and novel intermediates useful in the synthesis of pharmaceutically active compounds, in particular neutral endopeptidase (NEP) inhibitors.

BACKGROUND OF THE INVENTION

The present invention relates to a method to prepare N-acyl derivatives of biphenyl alanine. N-acyl derivatives of biphenyl alanine are key intermediates in the synthesis of pharmaceutically active compounds, in particular neutral endopeptidase (NEP) inhibitors, such as those described in U.S. Pat. No. 4,722,810, U.S. Pat. No. 5,223,516, U.S. Pat. No. 4,610,816, U.S. Pat. No. 4,929,641, South African Patent Application 84/0670, UK 69578, U.S. Pat. No. 5,217,996, EP 00342850, GB 02218983, WO 92/14706, EP 0034391 1, JP 06234754, EP 00361365, WO 90/09374, JP 07157459, WO 94/15908, U.S. Pat. No. 5,273,990, U.S. Pat. No. 5,294,632, U.S. Pat. No. 5,250,522, EP 00636621, WO 93/09101, EP 00590442, WO 93/10773, WO2008/031567 and U.S. Pat. No. 5,217,996.

Typically, synthetic methods to prepare biphenyl alanine derivatives use expensive starting materials such as non-natural D-tyrosine. Moreover, said methods require the use of trifluoromethanesulfonic anhydride, which is also expensive, to activate the phenolic hydroxyl in order to carry out the aryl coupling reaction leading to the desired biphenyl structure. One example of such a synthetic approach is described in the *Journal of Medicinal Chemistry* 1995, Vol. 38 No. 10. Scheme 1 illustrates one of these methods:

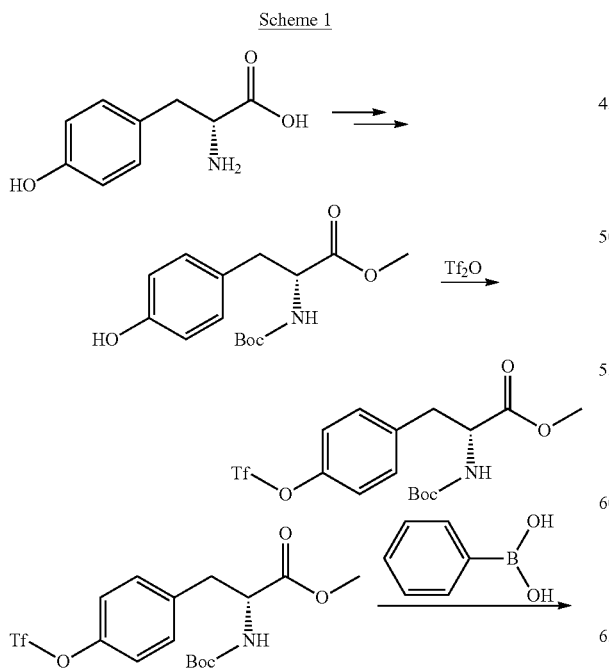

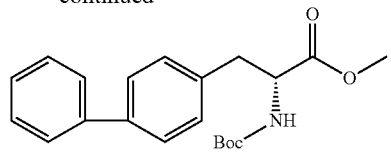

Therefore, there is a strong need to develop inexpensive methods to prepare biphenyl alanine derivatives. It is found that the present invention meets this objective and thus provides a process that is industrially advantageous.

SUMMARY OF THE INVENTION

This invention provides a method for preparing a N-acyl-biphenyl alanine of formula (3), as defined herein. The new process, according to the present invention, for producing compounds according to formula (3), is summarized in Scheme 2. By reacting biphenyl formaldehyde, as defined herein, N-acylglycine (A), as defined herein, and an anhydride (B), as defined herein, under alkaline conditions, a compound of formula (1), as defined herein, is obtained. Said compound of formula (1) is next converted into a compound of formula (2), as defined herein, which in turn is hydrogenated, for example with hydrogen and palladium on charcoal, to provide the compound of formula (3). A compound of formula (3) can be converted into a neutral endopeptidase (NEP) inhibitors, for example, as described in the Journal of Medicinal Chemistry, 1995, Vol. 38, No. 10, 1691, and the patent documents cited hereinbefore, the disclosure for each of which is incorporated by reference The synthetic process summarized in Scheme 2 uses inexpensive starting materials and reagents and is thus suitable for industrial production.

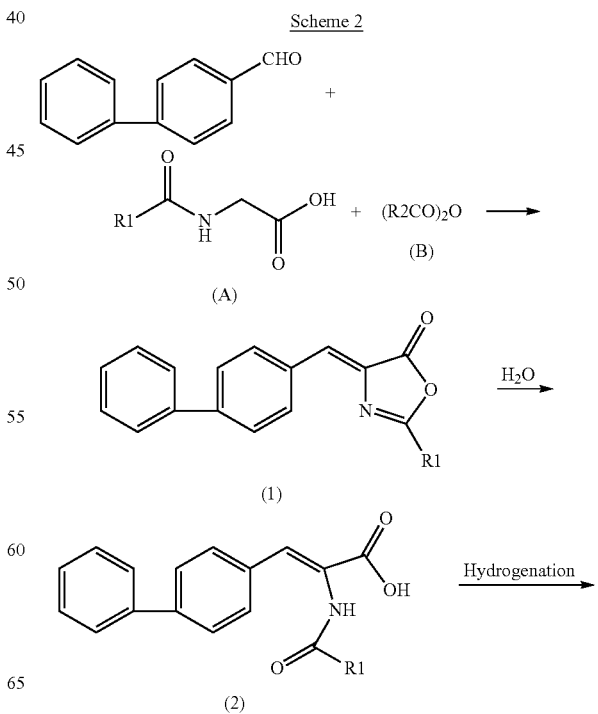

-continued

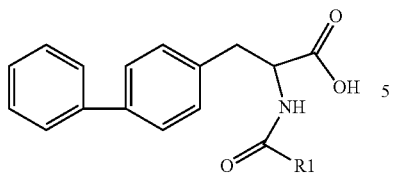

(3)

DETAILED DESCRIPTION OF THE INVENTION

Step a

In a first embodiment the present invention relates to a method for preparing a compound of formula (1-a), or salt thereof,

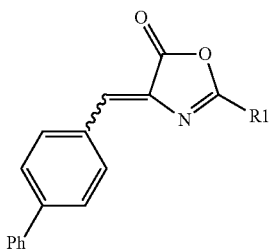

(1-a)

preferably wherein the compound of formula (1-a) is of the formula (1),

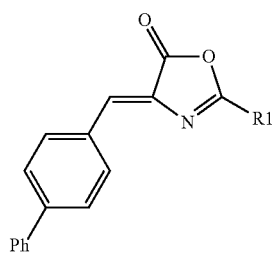

(1)

wherein R1 is $C_{1-7}$alkyl, preferably methyl, or $C_{6-10}$aryl, preferably phenyl, comprising reacting

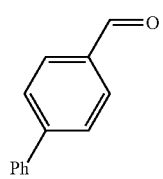

or salt thereof, with a compound of formula (A),

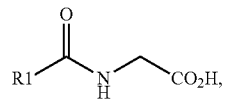

(A)

or salt thereof, wherein R1 is as defined for the compound of formula (1-a), and $(R2CO)_2O$, wherein R2 is $C_{1-2}$alkyl, preferably methyl or propyl, most preferably methyl or ethyl, under alkaline conditions, to provide the compound of formula (1-a).

The reactions described above can be carried out in solvents generally known in the art, for example, in the presence of a solvent, (named solvent I), selected from benzene, toluene, xylene, chlorobenzene, dichlorobenzene, nitrobenzene, heptane, acetic acid, propionic acid, isobutyric acid, n-butyric acid, acetic anhydride or propionic anhydride.

Preferably, anhydride (B) is acetic anhydride or propionic anhydride.

The term "under alkaline conditions" means that the step requires a base. Preferably, said base is selected from triethylamine, pyridine, N-methylpyrrole, N-methylmorpholine, sodium bicarbonate, sodium carbonate, potassium bicarbonate, potassium carbonate, sodium acetate, potassium acetate, sodium propionate, or potassium propionate.

Preferably, step a is carried out at a reaction temperature of from 80 deg C. to reflux, preferably, with a reaction time of 0.5 to 48 hours.

Preferably, in step a, the molar ratio of said biphenyl formaldehyde:said N-acylglycine (A):said anhydride (B):said base is 1.0:(0.7 to 5.0):(1.0 to 6.0):(0.05 to 2.00); the amount of said solvent I is 0 to 20 times the weight of feed amount of said biphenyl formaldehyde.

Step b

In a further embodiment, the present invention relates to a method for preparing a compound of formula (2-a), or salt thereof,

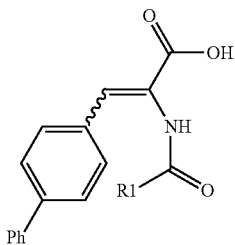

(2-a)

preferably wherein the compound of formula (2-a) is of the formula (2),

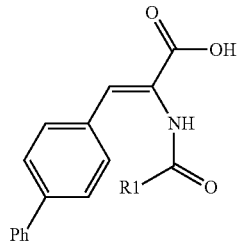

(2)

wherein R1 is $C_{1-7}$alkyl, preferably methyl, or $C_{6-10}$aryl, preferably phenyl,
comprising
reacting
a compound of formula (1-a), or salt thereof,

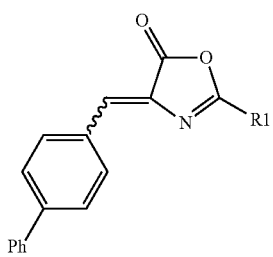

(1-a)

preferably wherein the compound of formula (1-a) is of the formula (1),

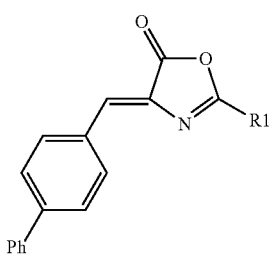

(1)

wherein R1 is as defined for a compound of formula (2-a), with water
to provide the compound of formula (2-a).

The reactions described above can be carried out in solvents generally known in the art, for example, in the presence of a solvent, (named solvent II), selected from water, ethanol, methanol, isopropanol, propanol, ethyl acetate, isopropyl acetate, ethyl propionate, acetone, butanone, methyl isobutyl ketone, tetrahydrofuran, 1,4-dioxane, N, N-dimethyl formamide, or N-methylpyrrole. Preferably, the weight of feed amount of said solvent II is 2 to 50 times the amount of the compound of formula (1) [named product 1] in step a; the weight of feed amount of water is 0.5 to 20 times the amount of product 1 in step a.

Preferably, step b is carried out at a reaction temperature of from room temperature to reflux.

Step c

In a further embodiment, the present invention relates to a method for preparing a compound of formula (3), or salt thereof,

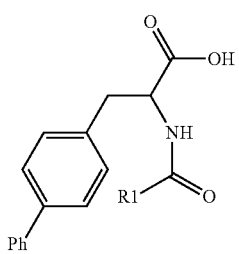

(3)

preferably wherein the compound of formula (3) is of the formula (3-a),

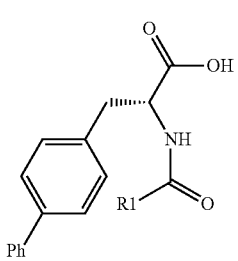

(3-a)

wherein R1 is $C_{1-7}$alkyl, preferably methyl, or $C_{6-10}$aryl, preferably phenyl,
comprising
treating a compound of formula (2-a), or salt thereof, (2-a)

preferably wherein the compound of formula (2-a) is of the formula (2),

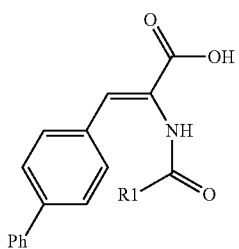

(2)

wherein R1 is $C_{1-7}$alkyl, preferably methyl, or $C_{6-10}$aryl, preferably phenyl,
under hydrogenation conditions
to provide the compound of formula (3).

Hydrogenation conditions are well-known in the art and thus refer to the use of hydrogen and a transition metal catalyst, for example, as described in Section B.3.3 in WO2009/090251, which is incorporated herein by reference. Preferably the transition metal catalyst is palladium, preferably palladium on charcoal, preferably containing 1% to 20% palladium by weight.

In another embodiment, the hydrogenation takes place with hydrogen in the presence of a transition metal catalyst comprising an organometallic complex and a chiral ligand, for example as described in Section C.2 in WO2009/090251, which is incorporated herein by reference.

The reactions described above can be carried out in solvents generally known in the art, for example, in the presence of a solvent (named solvent III) selected from ethanol, methanol, ethyl acetate, N, N-dimethyl formamide, N-methylpyrrole and tetrahydrofuran.

Preferably, in step c, the weight of feed amount of said solvent III is 5 to 50 times of the amount of the compound of formula (1) [named product 1] in step a. Preferably, the amount of palladium on charcoal is 0.1% to 20% of the compound of formula (2) [named product 2] in step b by weight.

Preferably, in step c, glacial acetic acid is also added in order to maintain acidic conditions.

Preferably, the reaction temperature is of from 20 deg C. to 150 deg C.

Preferably, the pressure of hydrogen is 0.2 MPa to 10.0 MPa.

Further Embodiments

In a further aspect, the present invention relates to a method for preparing a compound of formula (3), as defined herein, or salt thereof, comprising
  i) step a), as described above;
  ii) step b), as described above; and
  iii) step c) as described above.

In a still further aspect, the present invention relates to a method for preparing a compound of formula (3), as defined herein, or salt thereof, comprising
  iv) step b), as described above; and
  v) step c) as described above.

Preferred Embodiments

Embodiment [1]

A method for preparing N-acylbiphenyl alanine which is characterized by the following steps:

a.

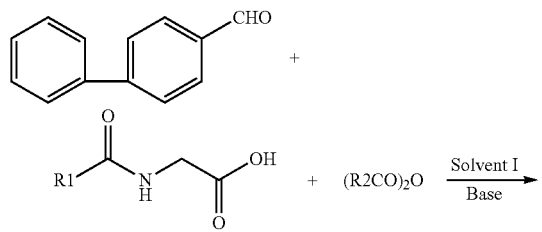

b.

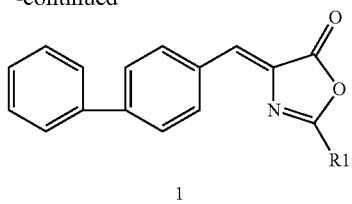

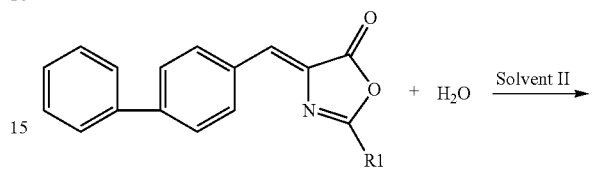

c.

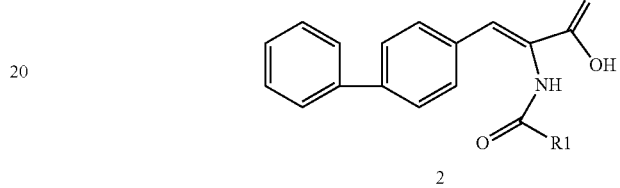

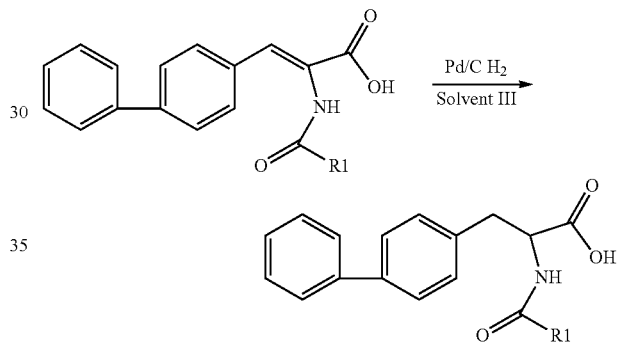

Wherein R1 is a straight-chain or branched-chain alkyl or aryl and R2 is a methyl or ethyl.

Embodiment [2]

A method for preparing N-acylbiphenyl alanine according to embodiment [1], characterized in that for step a, the molar ratio of said biphenyl formaldehyde:said N-acylglycine:said anhydride:said base is 1.0:(0.7 to 5.0):(1.0 to 6.0):(0.05 to 2.00), and the amount of said solvent I is 0 to 20 times the weight of feed amount of said biphenyl formaldehyde.

Embodiment [3]

A method for preparing N-acylbiphenyl alanine according to embodiment [1], characterized in that for step a, said solvent I is selected from benzene, toluene, xylene, chlorobenzene, dichlorobenzene, nitrobenzene, heptane, acetic acid, propionic acid, isobutyric acid, n-butyric acid, acetic anhydride, or propionic anhydride; said anhydride is acetic anhydride or propionic anhydride; said base is selected from triethylamine, pyridine, N-methylpyrrole, N-methylmorpholine, sodium bicarbonate, sodium carbonate, potassium bicarbonate, potassium carbonate, sodium acetate, potassium acetate, sodium propionate, or potassium propionate.

Embodiment [4]

A method for preparing N-acylbiphenyl alanine according to embodiment [1], characterized in that step a is carried out at a reaction temperature from 80 deg C. to reflux with a reaction time of 0.5 to 48 hours.

Embodiment [5]

A method for preparing N-acylbiphenyl alanine according to embodiment [1], characterized in that for step b, said solvent II is selected from water, ethanol, methanol, isopropanol, propanol, ethyl acetate, isopropyl acetate, ethyl propionate, acetone, butanone, methyl isobutyl ketone, tetrahydrofuran, 1,4-dioxane, N, N-dimethyl formamide, or N-methylpyrrole.

Embodiment [6]

A method for preparing N-acylbiphenyl alanine according to embodiment [1], characterized in that for step b, the weight of feed amount of said solvent II is 2 to 50 times the amount of product 1 in step a; the feed amount of said water is 0.5 to 20 times the amount of product 1 in step a.

Embodiment [7]

A method for preparing N-acylbiphenyl alanine according to embodiment [1], characterized in that step b is carried out at a reaction temperature from room temperature to reflux.

Embodiment [8]

A method for preparing N-acylbiphenyl alanine according to embodiment [1], characterized in that for step c, the said solvent III is selected from ethanol, methanol, ethyl acetate, N, N-dimethyl formamide, N-methylpyrrole, or tetrahydrofuran; and said palladium charcoal contains 1% to 20% palladium by weight.

Embodiment [9]

A method for preparing N-acylbiphenyl alanine according to embodiment [1], characterized in that for step c, wherein the weight of feed amount of said solvent III is 5 to 50 times the amount of product 1 in step a, the amount of said palladium charcoal is 0.1% to 20% of the product 2 in step b by weight.

Embodiment [10]

A method for preparing N-acylbiphenyl alanine according embodiment [1], characterized in that glacial acetic acid is also added in order to adjust pH and maintain acidic conditions while step c is carried out, and the range of reaction temperature is from 20 deg C. to 150 deg C., and said pressure of hydrogen is 0.2 MPa to 10.0 MPa.

GENERAL TERMS

Listed below are definitions of various terms used to describe the present invention. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

Alkyl being a radical or part of a radical is a straight or branched (one or, if desired and possible, more times) carbon chain, and is especially $C_1$-$C_7$-alkyl, such as $C_1$-$C_4$-alkyl, in particular branched $C_1$-$C_4$-alkyl, such as isopropyl. The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl, in particular methyl, ethyl, n-propyl, iso-propyl, n-butyl, isobutyl, sec-butyl, tert-butyl. Very preferred is methyl or ethyl.

Aryl, as a radical or part of a radical, for example is a mono- or bicyclic aryl with 6 to 22 carbon atoms, such as phenyl, indenyl, indanyl or naphthyl, in particular phenyl.

In formulae above and below, the term " ⌇ " represents a covalent bond, which comprises an (E) stereoisomer as well as a (Z) stereoisomer.

The term "reflux" refers to the temperature at which the reaction mixture boils, preferably a temperature up to 180° C., preferably up to 140° C.

As used herein, the term "room temperature" or "ambient temperature" means a temperature of from 20 to 35° C., such as of from 20 to 25° C.

The terms "transition metal catalyst", "organometallic complex" and "chiral ligand" are as described in WO2009/090251, and said definitions are incorporated herein by reference.

In the formulae of the present application the term "Ph" means phenyl.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter, is to be understood as referring also to one or more salts thereof or a mixture of a corresponding free compound, intermediate or starting material and one or more salts thereof, each of which is intended to include also any solvate, metabolic precursor such as ester or amide, or salt of any one or more of these, as appropriate and expedient and if not explicitly mentioned otherwise. Different crystal forms may be obtainable and then are also included. Salts can be formed where salt forming groups, such as basic or acidic groups, are present that can exist in dissociated form at least partially, e.g. in a pH range from 4 to 10 in aqueous solutions, or can be isolated especially in solid, especially crystalline, form. In the presence of basic groups (e.g. imino or amino), salts may be formed preferably with organic or inorganic acids. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid. In the presence of negatively charged radicals, such as carboxy or sulfo, salts may be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine. When a basic group and an acid group are present in the same molecule, internal salts may also be formed. Particularly useful salts include the hydrochloric acid, hydrobromic acid, sulfuric acid, nitric acid, phosphoric, lactic acid, fumaric acid, succinic acid, oxalic acid, malic acid, malonic acid, tartaric acid, tolyltartaric acid, benzoyltartaric acid, orotic acid, nicotinic acid, methane-sulfonic acid or 4-methylbenzenesulfonic acid salts of compounds of formula (1), (1-a), (2), (2-a), (3), (3-a) and the like formed from reaction with the above reagents. Methods to prepare acid addition salts are described in the literature, for example, in the relevant chapters of "CRC Handbook of Optical Resolutions via Diasteromeric Salt Formation", D. Kozma, CRC Press 2002, in Acta Cryst, 2006, B62, 498-505 and in Synthesis, 2003, 13, 1965-1967.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

Particular embodiments of the invention are provided in the following Examples. These Examples serve to illustrate the invention without limiting the scope thereof, while they on the other hand represent preferred embodiments of the reaction steps, intermediates and/or the process of the present invention.

Example 1

Synthesis of 4-(4-biphenyl methylene)-2-methyl-oxazole-5 (4H)-ketone (1, R1=Me)

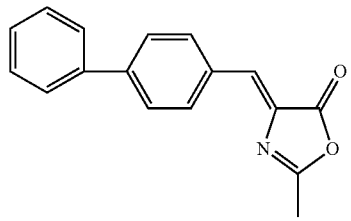 [SMILES: CC1=N/C(=C\c2ccc(-c3ccccc3)cc2)C(=O)O1]

In a dry and clean reaction bottle, add 36.4 g of biphenyl formaldehyde (Japan, Mitsubishi Chemical Co, Ltd, industrial, contents>98%), 28 g of acetyl glycine, 56 g of acetic anhydride, and 6 g of anhydrous sodium acetate. Heat to reflux for 0.5 hours. End heat preservation and cool to 80 deg C. Add 200 ml of water and agitate for 30 min. Filtrate and use 100 ml of water to wash filter cake for two times. Vacuum dry wet product at 30 to 40 deg C. to obtain the title product.

1H NMR (400 MHz, CDCl$_3$) δ 8.16 (d, J=8.4 Hz, 2H), 7.74-7.66 (m, 2H), 7.66-7.58 (m, 2H), 7.52-7.43 (m, 2H), 7.43-7.36 (m, 1H), 7.19 (s, 1H), 2.43 (s, 3H). M=263.

Example 2

Synthesis of 2-acetamido-3-biphenyl propenoic acid (2, R1=Me)

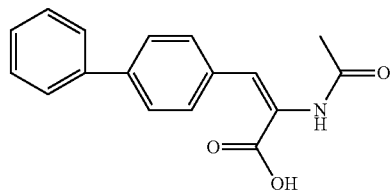 [SMILES: CC(=O)N/C(=C/c1ccc(-c2ccccc2)cc1)C(=O)O]

In a 1000 ml reaction bottle, add 40 g of 4-(4-biphenyl methylene)-2-methyl-oxazole-5 (4H)-ketone (1, R1=Me), 450 ml of acetone, and 60 ml of tap water. Heat to reflux for 8 hours. End heat preservation. Add 3 g activated charcoal and decolorate for 1 hour. Filtrate and wash with 50 ml of acetone. Steam distillate acetone about 300 ml and then add 200 ml of water. Cool down to 20 deg C. Filtrate and dry wet product at 60 deg C. to obtain the title product.

1H NMR (400 MHz, DMSO) δ 12.69 (s, 1H), 9.53 (s, 1H), 7.81-7.64 (m, 6H), 7.49 (dd, J=10.4, 4.7 Hz, 2H), 7.39 (dd, J=8.2, 6.5 Hz, 1H), 7.26 (s, 1H), 2.01 (s, 3H). M=281, M+=280.

Example 3

Synthesis of 3-biphenyl-2-acetamido alanine acid (3, R1=Me)

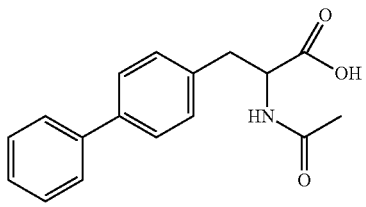 [SMILES: CC(=O)NC(Cc1ccc(-c2ccccc2)cc1)C(=O)O]

In a 1 L high-pressure autoclave, add 20 g of 2-acetamido 3-biphenyl propenoic acid (2, R1=Me), 300 ml of anhydrous ethanol, 2 ml of glacial acetic acid, and 1 g of palladium charcoal containing 5% of palladium. Seal the reaction autoclave and use nitrogen to displace air. Heat to 70 to 80 deg C. of internal temperature. Adjust hydrogen pressure to 6 MPa. React for 20 hours with heat preservation. Cool down reaction autoclave to 60 deg C. Release gas. Filtrate it. Wash with 10 ml of ethanol. Condense the filtrate to about 60 ml. Cool down to 0 to 5 deg C. Filtrate and dry wet product at 60 deg C. to obtain the title product.

1H NMR (500 MHz, DMSO-d6): 1.82, 2.89-2.93, 3.08-3.12, 4.45-4.50, 7.33-7.37, 7.44-7.47, 7.58-7.60, 7.64-7.66, 8.26-8.28, 12.75; MS (m/z): 224.07 (100), 167.14 (56), 165.16 (26), 282.94 ([MH+], 1).

Example 4

Synthesis of 4-(4-biphenyl methylene)-2-phenyl-oxazole-5(4H)-ketone (1, R1=Ph)

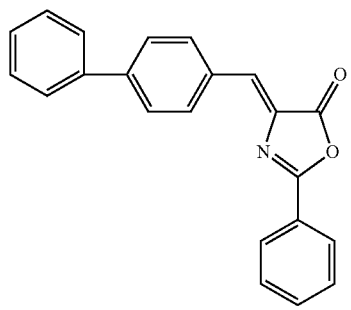 [SMILES: O=C1OC(c2ccccc2)=N/C1=C\c1ccc(-c2ccccc2)cc1]

In a dry and clean reaction bottle, add 36.4 g of biphenyl formaldehyde (Japan, Mitsubishi Chemical Co, Ltd, industrial, contents>98%), 33 g of N-benzoyl glycine, 52 g of propionic anhydride, and 20 g of N-methylmorpholine and 182 g of chlorobenzene. Heat to 100 deg C. Heat preserve for 24 hours. Cool down to 80 deg C. Add 200 ml of water and agitate for 30 min. Filtrate and use 100 ml of water to wash filter cake for two times. Vacuum dry wet product to obtain the title product.

1H NMR (400 MHz, CDCl3) δ 8.29 (d, J=8.4 Hz, 2H), 8.24-8.17 (m, 2H), 7.73 (d, J=8.4 Hz, 2H), 7.69-7.59 (m, 3H), 7.55 (t, J=7.5 Hz, 2H), 7.49 (dd, J=10.2, 4.8 Hz, 2H), 7.44-7.37 (m, 1H), 7.29 (s, 1H). M=325.

Example 5

Synthesis of 2-benzamido-3-biphenyl propenoic acid (2, R1=Ph)

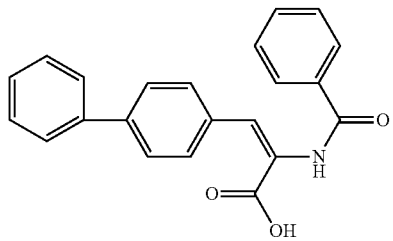 [SMILES: O=C(O)/C(=C\c1ccc(-c2ccccc2)cc1)NC(=O)c1ccccc1]

In a 1000 ml reaction bottle, add 60 g of 4-(4-biphenyl methylene)-2-phenyl-oxazole-5 (4H)-ketone (1, R1=Ph), 1000 ml of tetrahydrofuran, and 150 ml of tap water. Heat to room temperature. Heat preserve for 24 hours. Add 3 g of activated charcoal and decolorate for 1 hour. Filtrate and wash with 50 ml of tetrahydrofuran. After steam distillating about 600 ml of tetrahydrofuran, cool down to 20 deg C. Filtrate and dry wet product at 60 deg C. to obtain the title product.

1H NMR (400 MHz, DMSO) δ 9.61 (s, 1H), 8.00 (t, J=8.6 Hz, 2H), 7.82-7.36 (m, 13H), 7.33 (t, J=7.2 Hz, 1H). M=343, M+=342.

Example 6

Synthesis of 3-biphenyl-2-benzamido alanine (3, R1=Ph)

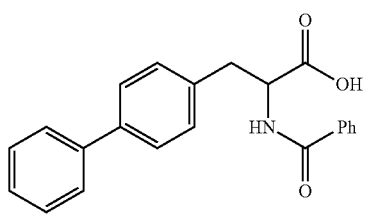 [SMILES: O=C(NC(Cc1ccc(-c2ccccc2)cc1)C(=O)O)c1ccccc1]

In a 1 L high-pressure autoclave, add 10 g of 2-benzamido 3-biphenyl propenoic acid (2, R1=Ph), 350 ml of methanol, 1 ml of glacial acetic acid, and 2 g of palladium charcoal (Pd/C) containing 5% of palladium. Seal the reaction autoclave and displace air with nitrogen. Heat to 140 to 150 deg C. of internal temperature. Adjust nitrogen pressure to 0.2 MPa. React for 20 hours with heat preservation. Cool down reaction autoclave to 60 deg C. Release gas. Filtrate and wash with about 10 ml of ethanol. Condense filtrate to about 60 ml. Cool down to 0 to 5 deg C. Filtrate and dry wet product at 60 deg C. to obtain the title product.

1H NMR (500 MHz, DMSO-d6): 3.12-3.17, 3.23-3.27, 4.65-4.70, 7.31-7.33, 7.34-7.45, 7.46-7.48, 7.58-7.60, 7.62-7.64, 7.83-7.84, 8.77-8.79, 12.85; MS (m/z): 224.0 (100), 167.1 (34), 165.1 (15), 105.1 (10), 77.2 (18), 344.8 ([MH+], 1).

Example 7

Synthesis of 4-(4-biphenyl methylene)-2-phenyl-oxazole-5(4H)-ketone (1, R1=Ph)

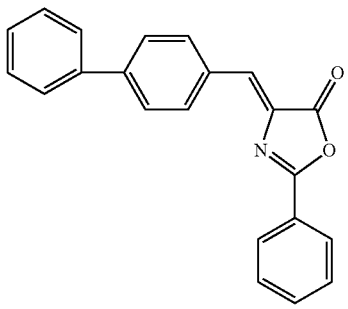 [SMILES: O=C1OC(c2ccccc2)=N/C1=C\c1ccc(-c2ccccc2)cc1]

In a dry and clean reaction bottle, add 36.4 g of biphenyl formaldehyde (Japan, Mitsubishi Chemical Co, Ltd, industrial, contents>98%), 33 g of N-benzoyl glycine, 52 g of propionic anhydride, and 10 g of anhydrous sodium propionate and 200 g of dichlorobenzene. Heat to 80 deg C. Heat preserve for 48 hours. Cool down to 80 deg C. Add 200 ml of water and agitate for 30 min. Filtrate and use 100 ml of water to wash filter cake two times. Vacuum dry wet product at 30 to 40 deg C. to obtain the title product.

Spectroscopic data as Example 4.

Example 8

Synthesis of 2-benzamido-3-biphenyl propenoic acid (2, R1=Ph)

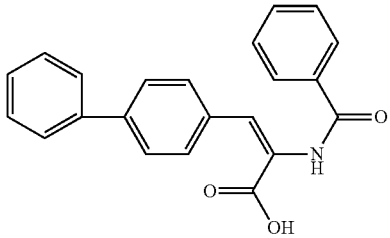 [SMILES: O=C(O)/C(=C\c1ccc(-c2ccccc2)cc1)NC(=O)c1ccccc1]

In a 1000 ml reaction bottle, add 50 g of 4-(4-biphenyl methylene)-2-phenyl-oxazole-5 (4H)-ketone (1, R1=Ph), 550 ml of butanone, and 120 ml of tap water. Heat to 40 deg C. Heat preservation for 24 hours. Add 3 g of activated charcoal and decolorate for 1 hour. Filtrate and wash with 50 ml of tetrahydrofuran. After steam distillating about 600 ml of tetrahydrofuran cool down to 20 deg C. Filtrate and dry wet product at 60 deg C. to obtain the title product.

Spectroscopic data as Example 5.

Example 9

Synthesis of 3-biphenyl-2-benzamido alanine (3, R1=Ph)

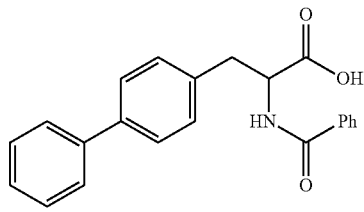 [SMILES: O=C(NC(Cc1ccc(-c2ccccc2)cc1)C(=O)O)c1ccccc1]

In a 1 L high-pressure autoclave, add 15 g of 2-benzamido 3-biphenyl propenoic acid (2, R1=Ph), 300 ml of tetrahydrofuran, 1.5 ml of glacial acetic acid, and 4 g of palladium charcoal (Pd/C) containing 5% of palladium. Seal the reaction autoclave and displace air with nitrogen. Heat to 100 to 110 deg C. of internal temperature. Adjust hydrogen pressure to 10.0 MPa. React for 20 hours with heat preservation. Cool down reaction autoclave to 60 deg C. Release gas. Filtrate and wash with about 10 ml of ethanol. Condense filtrate to about 60 ml. Cool down to 0 to 5 deg C. Filtrate and dry wet product at 60 deg C. to obtain the title product.

Spectroscopic data as Example 6.

The invention claimed is:

1. A process for preparing a compound of formula (3), or salt thereof,

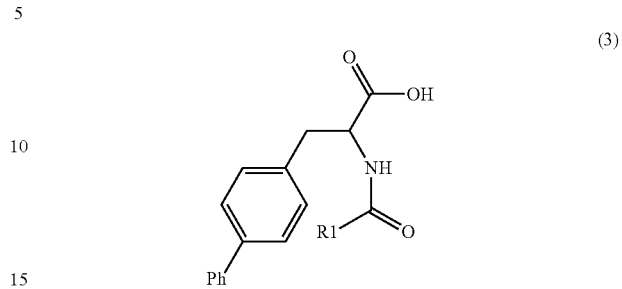

(3)

wherein R1 is $C_{1-7}$alkyl, or $C_{6-10}$aryl, comprising treating a compound of formula (2-a), or salt thereof,

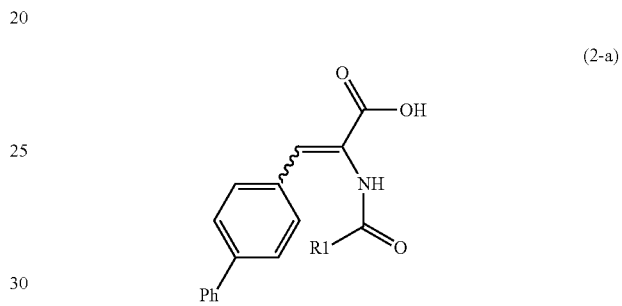

(2-a)

wherein R1 is $C_{1-7}$alkyl, or $C_{6-10}$aryl, under hydrogenation conditions to provide the compound of formula (3).

2. The process according to claim 1 wherein the compound of formula (3) is of the formula (3-a),

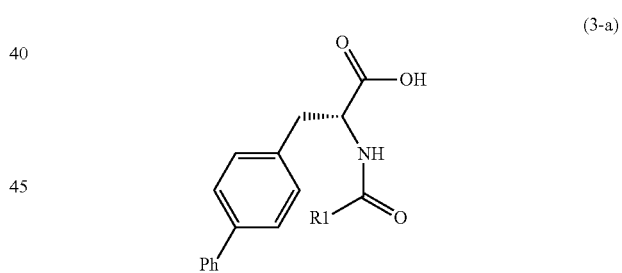

(3-a)

wherein R1 is $C_{1-7}$alkyl or $C_{6-10}$aryl, and
wherein the compound of formula (2-a) is of the formula (2),

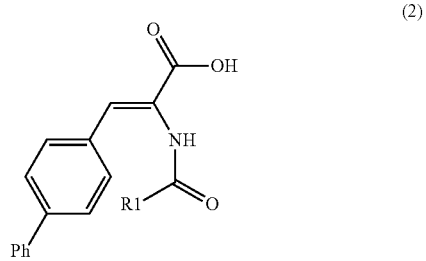

(2)

wherein R1 is $C_{1-7}$alkyl, or $C_{6-10}$aryl.

3. The process according to claim 1, wherein
in the compound of formula (3-a) or of formula (3) R1 is methyl or phenyl, and
in the compound of formula (2-a) or of formula (2) R1 is methyl or phenyl.

4. The process according to claim 1, wherein the hydrogenation conditions comprise the use of hydrogen and palladium, and the palladium can be present with charcoal.

5. The process for preparing a compound of formula (3) according to claim 1, wherein the compound of formula (2-a) or salt thereof,

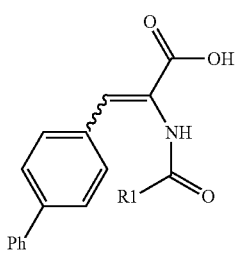

(2-a)

wherein R1 is C$_{1-7}$alkyl, or C$_{6-10}$aryl, is prepared by a process comprising reacting a compound of formula (1-a), or salt thereof,

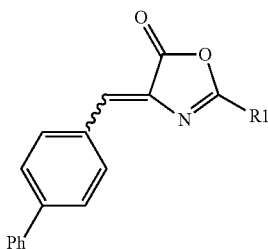

(1-a)

wherein R1 is as defined for a compound of formula (2-a), with water to provide the compound of formula (2-a).

6. The process according to claim 5, wherein the compound of formula (2-a) is of the formula (2),

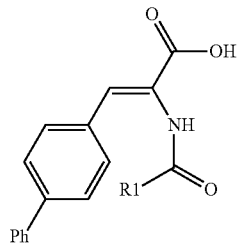

(2)

wherein R1 is C$_{1-7}$alkyl, or C$_{6-10}$aryl, and
wherein the compound of formula (1-a) is of the formula (1),

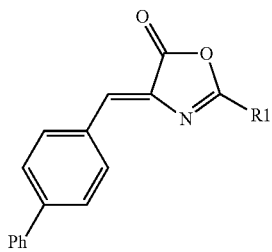

(1)

wherein R1 is as defined for a compound of formula (2-a).

7. The process according to claim 5, wherein in the compound of formula (2-a) or of formula (2) R1 is methyl or phenyl.

8. The process according to claim 5, wherein the reaction is carried out at a temperature of from room temperature to reflux temperature.

9. The process for preparing a compound of formula (3) according to claim 5, wherein the compound of formula (1-a), or salt thereof,

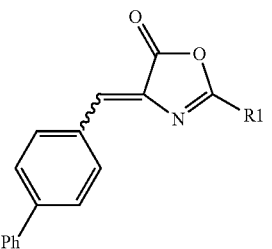

(1-a)

wherein R1 is C$_{1-7}$alkyl, or C$_{6-10}$aryl, is prepared by a process comprising reacting

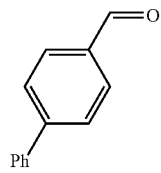

or salt thereof, with a compound of formula (A), or salt thereof,

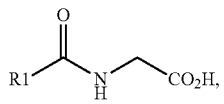

(A)

wherein R1 is as defined for the compound of formula (1-a), and
(R2CO)$_2$O, wherein R2 is C$_{1-7}$alkyl, under alkaline conditions, to provide the compound of formula (1-a).

10. The process according to claim 9, wherein the compound of formula (1-a) is of the formula (1),

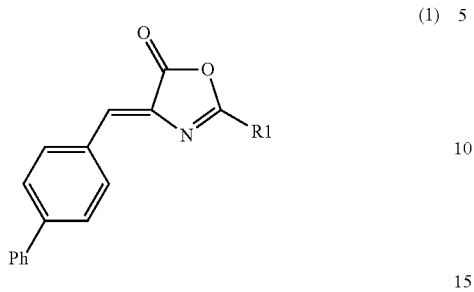

(1)

wherein R1 is $C_{1-7}$alkyl or $C_{6-10}$aryl.

11. The process according to claim 9, wherein
in the compound of formula (1-a) or of formula (1), R1 is methyl or phenyl, and
in the compound of formula (R2CO)$_2$O, R2 is methyl or propyl.

12. The process according to claim 9, wherein the alkaline conditions comprise the use of a base selected from triethylamine, pyridine, N-methylpyrrole, N-methylmorpholine, sodium bicarbonate, sodium carbonate, potassium bicarbonate, potassium carbonate, sodium acetate, potassium acetate, sodium propionate and potassium propionate.

13. The process according to claim 9, wherein the reaction is carried out at a temperature of from of from 80 deg C. to reflux temperature.

* * * * *